United States Patent [19]

Bau et al.

[11] Patent Number: 4,893,496
[45] Date of Patent: Jan. 16, 1990

[54] TORSIONAL WAVE FLUID SENSOR AND SYSTEM

[75] Inventors: Haim H. Bau, Swarthmore; Jin O. Kim, Philadelphia, both of Pa.; Lawrence C. Lynnworth, Waltham; Toan H. Nguyen, Needham, both of Mass.

[73] Assignee: Panametrics, Inc., Waltham, Mass.

[21] Appl. No.: 257,714

[22] Filed: Oct. 14, 1988

[51] Int. Cl.⁴ .............................................. G01N 9/24
[52] U.S. Cl. .................................... 73/32 A; 73/151; 73/861.18
[58] Field of Search ................. 73/32 A, 54, 151, 155, 73/290 V, 592, 597, 861.18, 861.21

[56] References Cited

U.S. PATENT DOCUMENTS 4,193,291  3/1980  Lynnworth ........................ 73/32 A
4,524,610  6/1985  Fitzgerald et al. ................. 73/32 A

FOREIGN PATENT DOCUMENTS 628143  2/1963  Belgium ............................ 73/290 V

OTHER PUBLICATIONS

Langdon, R. M., "Vibratory . . . Transducers", The Marconi Review, Third Quarter, 1980.
Lynnworth, L. C., "Industrial Applications . . . Using Low Intensity Ultrasound", IEEE Trans. Sonics and Ultrasonics, Mar. 1975.

Primary Examiner—John Chapman
Assistant Examiner—Kevin D. O'Shea
Attorney, Agent, or Firm—Lahive & Cockfield

[57] ABSTRACT

A guided torsional wave sensor has a cross-section with a strong interaction of torsional wave energy and the surrounding fluid, such that a wave propagates in the sensor with a functional dependence on a single fluid characteristic. In one embodiment, the sensor body is optimized for fluid density. Diamond, polyhedral and curved-sided embodiments are described. In another embodiment, the sensor body responds to fluid viscosity. This embodiment is preferably hollow, and may include threaded, fractal or roughened surface features to enhance viscous coupling. Different systems include further sensors, sensors with portions of differing profile, and special mounting or activation structures.

46 Claims, 14 Drawing Sheets

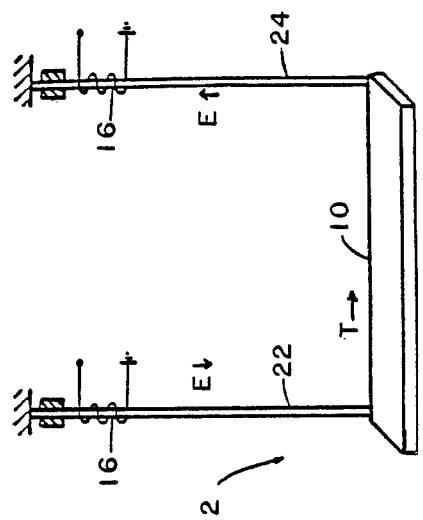
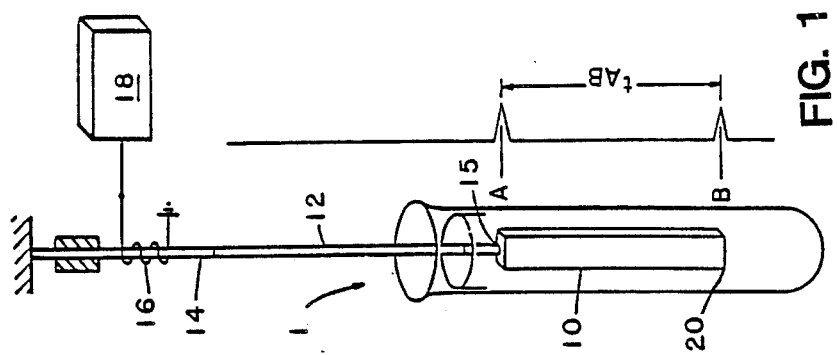
FIG. 1 (PRIOR ART)
FIG. 2 (PRIOR ART)

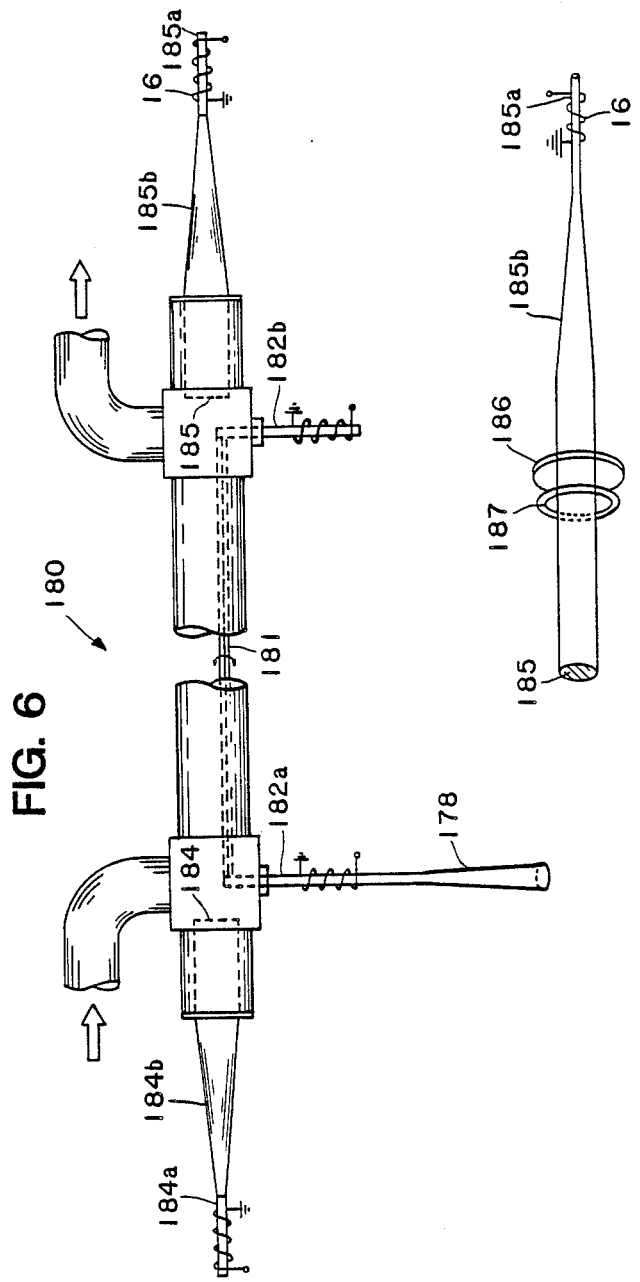

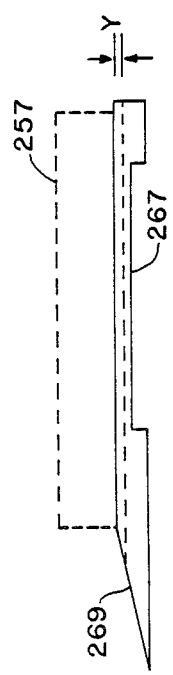
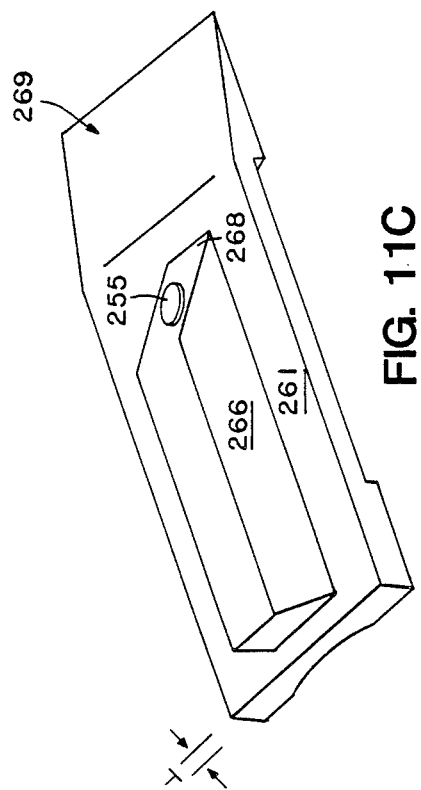
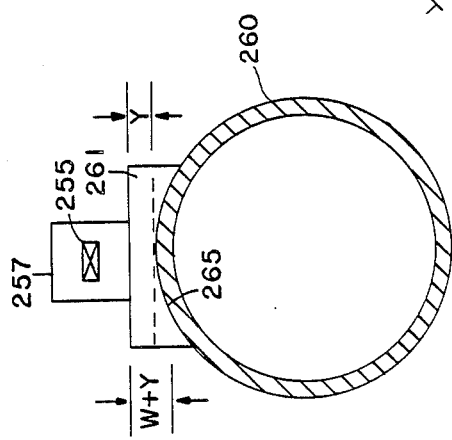
FIG. 11B
FIG. 11C
FIG. 11A

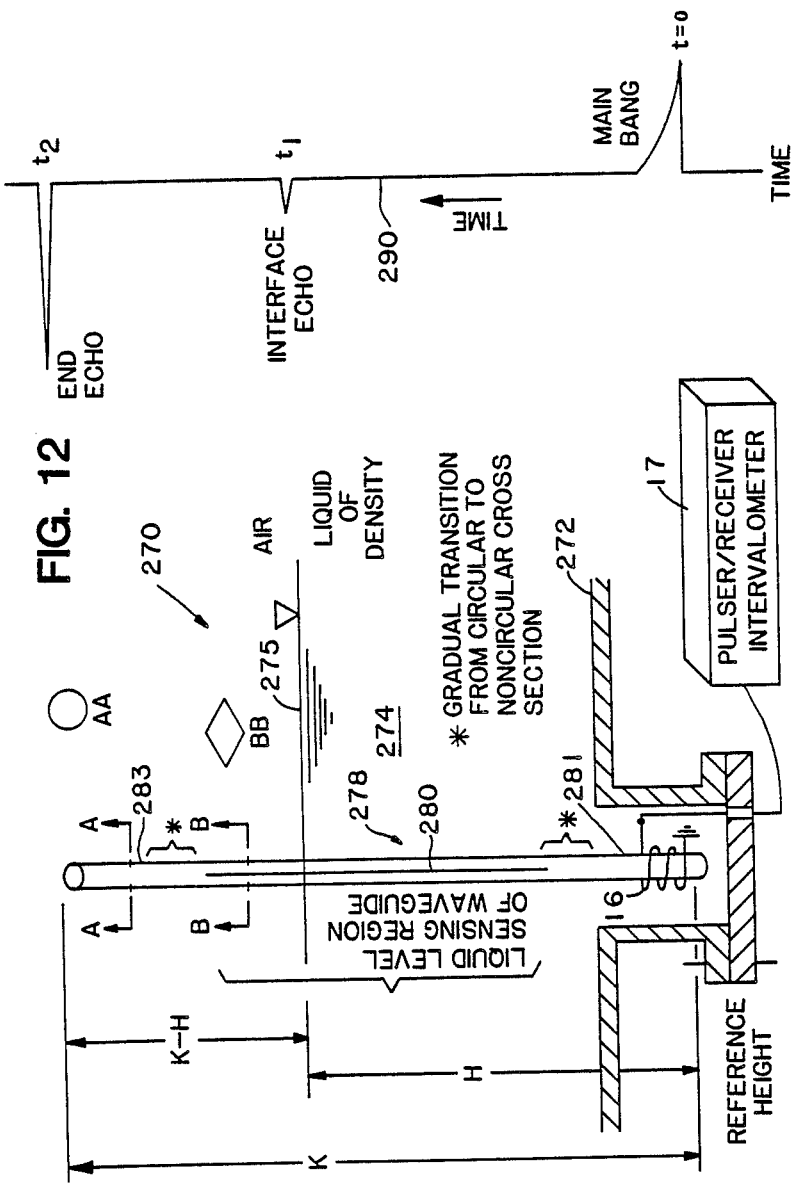

TORSIONAL WAVE FLUID SENSOR AND SYSTEM

Background of the Invention

This invention relates to apparatus for the measurement of a fluid characteristic by the propagation of wave energy along a sensor waveguide located in contact with the fluid, and, in particular, by the propagation of torsional wave energy in the sensor.

In such a device, the interaction of the guided wave energy with the fluid results in a lowered velocity of propagation along the sensor, so that the change in flight time of the wave, as compared to a reference time with the sensor in air or vacuum, provides an indication of a characteristic of the fluid in contact with the sensor. In particular circumstances where one or more of the fluid composition, container geometry and sensor characteristics are known, a measurement of flight time may provide an indication of a characteristic of the fluid such as fluid presence, fluid depth, fluid density or fluid temperature. A comprehensive description of possible transducer and sensor constructions and system configurations for torsional wave fluid sensing appears in U.S. Pat. No. 4,193,291 of inventor Lawrence C. Lynnworth. That patent shows a number of configurations that employ a sensor having a body of non-circular cross-section in which a torsional wave is propagated, and it describes particular examples, such as a strip of rectangular cross-section, for which the delay in flight time is a substantially linear function of fluid density.

The concept of using a non-circular sensor of relatively high aspect ratio to magnify the effect on propagation of torsional wave energy in a waveguide immersed in a surrounding fluid offers the prospect of greatly increasing the amount of flight time delay caused by the fluid, and hence increasing the sensitivity of the sensor to variations in fluid density. However, the lack of a good theoretical model for the sensor-fluid interaction, and the complex interdependence of the wave dynamics on density, viscosity and sensor geometry have limited the practical applications of torsional wave sensors.

More recently, applicant H. H. Bau has published a theory of torsional wave propagation (Torsional Wave Sensor-A Theory, H. H. Bau, J. Appl. Mech. Vol. 108, Dec. 1986). This theory was applied to obtain closed-form approximations of wave propagation for certain sensor cross-sections in an inviscid fluid, and these results were compared with earlier experimental results of Lynnworth obtained using rectangular sensors in such fluids, to validate that theory. That paper deals with elliptical and rectangular section sensors, for which mathematical solutions can be derived from results in the literature. As such, the theory is a first step toward analyzing the sensor-fluid interaction, in that it provides a basis for undertaking numerical analysis of the fluid coupling with different sensor cross sections. Such analysis can be expected to help optimize sensitivity to fluid density in situations where viscosity may be neglected.

Objects and Summary of the Invention

It is an object of the present invention to provide a torsional wave sensor optimized to respond to a fluid characteristic.

It is another object of the invention to provide a system for the torsional wave sensing of fluid characteristics wherein plural different torsional wave sensors respond selectively to different characteristics.

It is another or further object of the invention to provide systems wherein a torsional wave sensor assembly is mounted in a physical geometry to accurately detect a fluid characteristic while requiring a small number of physical openings or electrical connections to mount and operate the assembly.

It is another or further object of the invention to provide systems wherein a torsional wave sensor assembly has a geometry that provides enhanced signal separation and results in improved signal processing resolution.

One or more of these and other desirable objects are obtained in a sensor wherein a sensor body is at least partly immersed in a fluid and has a cross-section in which the propagation of torsional wave energy responds to the surrounding fluid. That is to say, the surrounding fluid affects wave propagation in a manner primarily dependent on a single fluid characteristic. In one embodiment, the sensor body has a non-circular cross-section and a shape responsive to fluid density. Diamond, polyhedral and curved-sided embodiments are described. In another embodiment, the sensor body is substantially of circular cross-section and responds to fluid viscosity. The surface of this latter embodiment preferably includes threaded, undulating, radially finned, fractal or roughened surface features to enhance viscous coupling.

A system employs a torsional wave sensor having selective sensitivity to one fluid characteristic, and at least one additional sensor. The additional sensor may be a torsional wave sensor responsive to a different characteristic, or a sensor of a different type, such as a conventional sensor which detects a related physical parameter like fluid height, temperature or propagation velocity. In one preferred system, two torsional wave sensors are fabricated as a single unit, with a first sensor body portion of one cross-sectional profile coupled to a second sensor body portion of a different cross sectional profile. A common transducer provides the torsional wave traveling in both body portions. A viscosity value is sensed by one sensor and applied to correct a density value sensed by the other, thus providing enhanced measurement of a wider range of real fluids. These fluids may include relatively inviscid fluids, and, more generally, visco-elastic fluids of diverse properties, such as viscous liquids of both Newtonian and non-Newtonian types.

Brief Description of Drawings

These and other features of the invention will be understood with reference to a discussion of the Figures, illustrating the principles of operation of the invention and a number of particular embodiments of torsional wave sensors and systems employing sensors according to the invention, as follows.

FIGS. 1 and 2 shows torsional wave sensors of the prior art;

FIGS. 6, 6A show another embodiment utilized for mass flow determinations;

FIGS. 10, 11A–11C show a preferred embodiment and further improvements of the system of FIG. 9;

FIG. 12 shows another sensor according to the invention adapted to a storage tank;

Detailed Description of Illustrated Embodiments

Torsional Wave Sensors

Figures 3A, 3B:
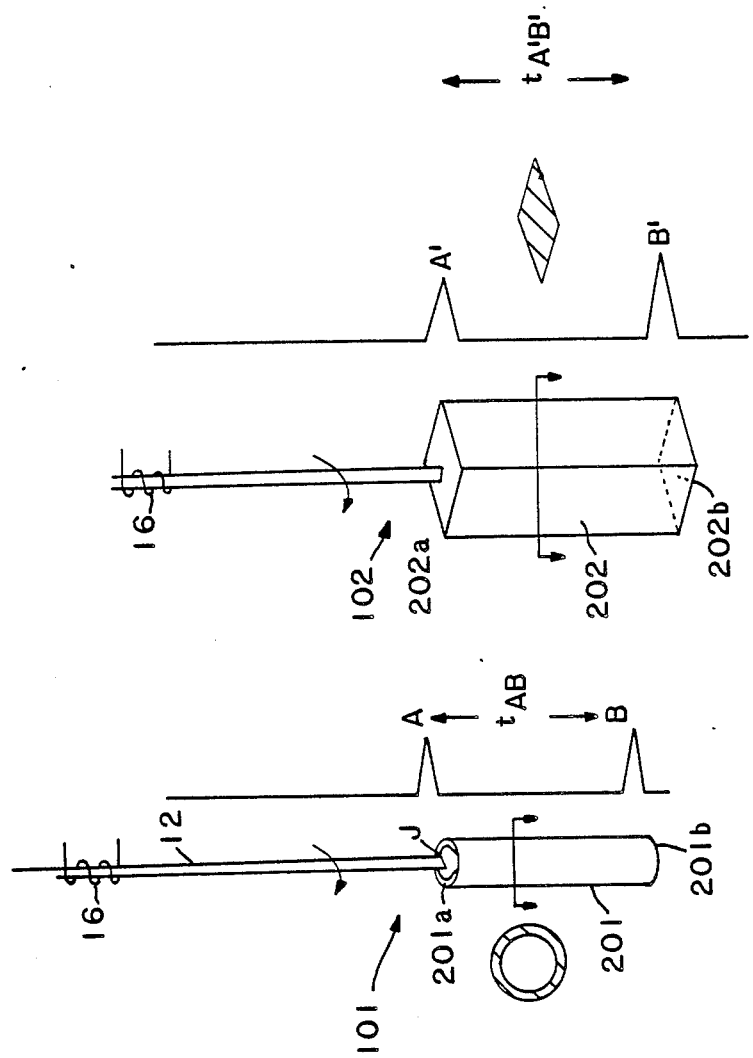
FIG. 3A shows a first embodiment of a sensor according to the invention optimized for sensing a first fluid characteristic.
FIG. 3B shows a second embodiment of a sensor according to the invention optimized for sensing a second fluid characteristic.

Before proceeding to a description of the invention, a brief discussion of torsional wave generation and sensing is in order, by way of general background. FIGS. 1 and 2 show two prior art systems wherein a sensor 1 includes a rectangular sensing body 10 which is immersed in a fluid and is actuated at one end to guide a torsional wave which propagates through the body 10 with a velocity that varies in a manner dependent on the surrounding fluid.

In FIG. 1, the torsional wave is provided by a torsional wave traveling in a lead-in exciter rod 12 which is axially attached to the sensor body 10, and the same rod is used to carry the echo of the torsional wave from the distal end 20 of the sensor body. The lead-in rod 12 is connected to a torsional wave generator/sensor assembly consisting of a magnetostrictive rod 14 surrounded by a coil 16 attached to an electronic instrument 18 such as a combined pulser/receiver and intervalometer. A continuous or pulsed DC electric current is passed axially along the rod 14 to maintain a circumferential magnetic field therein, and a current pulse is applied to coil 16 causing a time varying axial magnetic field to develop, which interacts with the circumferential field to exert a twisting force on rod 14, generating a torsional impulse. This is known as the Wiedemann effect. Similarly, the torsional echo returning along rod 12 to rod 14 induces an electromotive pulse in the coil (the "inverse Wiedemann effect") allowing detection of the return wave. FIG. 1 shows the trace of the electric signal corresponding to the echos A, B of the exciter pulse received from the top face 15 of sensor body 10 and the bottom face 20 of the sensor body, respectively. The interval $t_{AB}$ between the two echos is the flight time of the torsional wave in the shaped sensor body.

FIG. 2 shows another prior art transducer 2, having an alternative construction for exciting and sensing the torsional wave sensor body 10. In construction, a lead-in rod 22 applies wave energy to one end of the sensor body 10, and lead-out rod 24 leads out the wave energy appearing at the other end. Each rod 22, 24 has a junction at an edge of the end of a respective sensor body. In this construction, each rod carries an extensional wave, which is converted to or from a torsional wave in passing the junction between the rod and the sensor body. In this case, a simple coil 16 about the rod produces, or converts, the extensional wave in the rod to an electrical signal.

The exciter mechanisms 12, 14, 16 and 22, 24, 26 of FIGS. 1 and 2 are examples of convenient transducers for applying a torsional wave to a sensor body. Such a wave may also be created by an appropriate piezoelectric transducer element, or may be optically initiated by a laser pulse applied to a suitable structure. It will be understood in the following discussion that any such torsional wave transducer, or other known transducer having appropriate characteristics for the waveguide may be employed.

The foregoing two constructions employ a sensor body in the form of a strip of rectangular cross-section that serves as a waveguide for propagation of the torsional wave within the fluid. Earlier reported research of applicant Lynnworth has established the feasibility and enhanced sensitivity of such a torsional wave sensor for detecting fluid density as a function of flight time for certain fluids. The above-mentioned earlier reported research of applicant Bau has set forth a theoretical approximation which, for inviscid fluids in which the sensor cross-section induces only two-dimensional motion, relates wave velocity to a function of fluid density involving a number of constants that depend on sensor cross section, namely the sensor polar moment of inertia Is, the fluid apparent inertia $I_f$, and a constant K $=\sqrt{D/I_s}$ where D is the torsional rigidity of the sensor.

Applicant has developed a further theoretical analysis of the fluid-induced effects on guided torsional wave propagation, substantially as follows.

Theory

Consider a torsional stress wave traveling in a waveguide with a uniform cross section submerged in a liquid. As the torsional wave travels through the waveguide, the solid-liquid interface is alternately accelerated and decelerated. Consequently, the inertia that needs to be overcome by the torsional pulse is a combination of the solid waveguide's inertia ($I_s$) and the adjacent liquid's apparent inertia ($I_f$). To the first order approximation (Bau, 1986), the torsional wave speed (c) can be calculated from the equation:

$$c = K \left( \frac{G}{\rho_s} \right)^{1/2} \left( 1 + \frac{\rho_f I_f}{\rho_s I_s} \right)^{-1/2} \quad (1)$$

where G is the shear modulus of the solid, $K = °(D/I_s)$, and D is the torsional rigidity In experiments, applicant has measured the flight time of the torsional stress wave. Hence, it is desired to derive an expression for the effect of apparent inertia on the flight time Let $t_0$ and t denote, respectively, the flight time in air, which is assumed to be a good approximation for flight time in vacuum, and in liquid at the same temperature. $Dt = t - t_0$ denotes the difference in the transmission time of a wave in a waveguide submerged in liquid and one in air. From equation (1), with a good approximation:

$$\frac{Dt}{t_0} \approx \frac{\rho_f I_f}{2 \rho_s I_s} \quad (2)$$

When the waveguide has a non-circular cross-section, the fluid's motion is induced via the generation of a pressure field and a drag force. The pressure field is generated by the motion of the solid's surface which induces a normal velocity component in the fluid. The drag force results from viscous effects. Hence the apparent inertia of the fluid ($I_f$) can be taken as resulting from a combination of these two effects We denote the inviscid and viscous contributions to the apparent inertia as $I_{f,i}$ and $I_{f,v}$, respectively; that is, $I_f = I_{f,i} + I_{f,v}$. Only the inviscid inertia for rectangular and elliptical cross-sections of various ratios was calculated in Bau (1986).

Applicants Kim and Bau have subsequently calculated the inviscid inertia for other cross-sections (unpublished). The scale of the Pressure-induced flow field is of the same order of magnitude as the size of the waveguide's cross-section, so $I_{f,i}$ may be approximated by $C_1 I_s$, where $C_1$ is a constant of order one. $C_1$ depends on the cross section's geometry and aspect ratio. For example, for a rectangular cross section of aspect ratio 3.3, $C_l = 1.062$. The scale of the drag-induced flow-field is comparable to the thickness of the viscous boundary layer The thickness of the viscous boundary layer in a Newtonian fluid is of the order $(v/\omega)^{\frac{1}{2}}$, where $v = \mu/\rho f$ is the momentum diffusivity and $\omega$ is the wave's frequency. Hence, one would expect $I_{f,v}$ to be approximately $C_2 I_s (v/\omega a^2)^{\frac{1}{2}}$, where (a) is a characteristic dimension of the cross section and $C_2$ is a geometry-dependent constant.

Applicant has determined $C_2$ empirically. For example, for a rectangular waveguide with an aspect ratio of 3.3 and a=0.005 m, operating at a frequency $\omega = 50$ kHz at room temperature in water and glycerin, the values of $(u/w\, a^2)^{\frac{1}{2}}$ are approximately $2 \times 10^{-3}$ and $2 \times 10^{-2}$, respectively. Applicant has found that even in the latter case viscous effects contribute less than 10% to the fluid-induced inertia ($I_f$). Thus, in many circumstances, the viscous contribution is relatively small.

According to the above analysis, the apparent inertia of the fluid for a rectangular cross section sensor can be expressed as:

$$\frac{I_f}{I_s} = C_1 + C_2 \left(\frac{v}{\omega a^2}\right)^{1/2}. \quad (3)$$

On the other hand, when the waveguide's cross section is circular, there is only drag-induced apparent inertia (i.e., $C_1 = 0$). One approximation has been derived by Y. Wang (master's thesis, University of Pennsylvania, unpublished) for a e with cross sectional radius a, as:

$$\frac{I_f}{I_s} = \left(\frac{8v}{\omega a^2}\right)^{1/2}. \quad (4)$$

The constants $C_1$ and $C_2$ are fixed for any given sensor and they do not depend on the adjacent liquid.

From the foregoing discussion, it follows that from the flight time of a torsional wave measured in two different waveguides, each sensitive to substantially only one component of $I_f$, for example, waveguides with circular and non-circular (e.g., rectangular) cross sections, one can obtain both the density ($\rho f$) and the viscosity ($\mu$) of the fluid in which the sensors are immersed.

Practical Embodiments

From the foregoing theoretical considerations, applicant has developed practical embodiments which may be characterized in three general classes. First, there are sensors having a torsional-wave guiding sensor body with a cross-section which is primarily or strongly coupled to the fluid by inviscid coupling phenomena. One such cross-section that applicant has found by computer-simulated analysis and confirmed by experiments is a diamond cross-section, which applicant has found to present $\rho f$ sensitivity markedly superior to previously known torsional wave sensors. Second, there are sensor body cross-sections that are optimized to respond only to the viscous component $I_{f,v}$ of the apparent inertia. These include substantially circular cross-sections, especially ones having a threaded, undulating, radially-finned, roughened or fractally enhanced fluid-contacting surface. Third, there are systems that employ at least one torsional wave $I_f$-component responsive sensor. Optimized torsional waveguide sensors which respond strongly and primarily to either $\rho$ or viscosity will be generally referred to hereafter simply as density sensors and viscosity sensors. These systems may include systems with one of each type sensor, in which a viscosity sensor provides a lower-order correction term for the density sensor, or vice-versa. The contemplated systems also include systems wherein a guided torsional wave density or viscosity sensor is corrected by a measurement such as a temperature or fluid height measurement, which derived from an entirely different and possibly conventional sensing element, such as a thermistor or a fluid transit time transducer arrangement.

For non-Newtonian fluids, the invention further contemplates systems wherein a locally-sensed viscosity measurement together with a flow velocity measurement are empirically correlated to determine the effective free-stream viscosity. Further, in cases where the fluid density $\rho$, viscosity $\eta$ and flow velocity V are determined in a conduit of diameter D, the invention contemplates a system that calculates the Reynolds number Re as Re = $\rho$VD/$\eta$. Another system employs an extensional wave component of the energy travelling in the sensor body to derive a direct measure of temperature.

In the Figures discussed below, density and viscosity sensors according to the invention are illustrated for clarity as sensors having a diamond-or threaded-cylinder section, in accordance with presently preferred particular sensor embodiments It will be understood, however, that in accordance with applicant Bau's theory and practical simulations of fluid-sensor torsional wave coupling, other cross-sectional profiles are included within the scope of the invention. These profiles include composite cross-sections such as a hollow diamond shape. It will be further understood that the density of the sensor need not be uniform. For example, anti-fouling or anti-corrosion coatings of gold or teflon are contemplated, and the sensor may exhibit a density which diminishes stepwise, or continuously and monotonically, as a function of radial distance from the sensor axis. Further, variations of the highly density-sensitive diamond profile are contemplated. For example, by forming a diamond-profile sensor having concave, rather then linear, sides, a lesser polar moment of inertia is achieved and an increase in sensitivity may be expected in some operating conditions. In general, variations of a basic diamond profile are referred to herein as "diamond-like" sections.

FIG. 3A shows a viscosity sensor 101 according to the invention, having a sensor body 201 with an aspect ratio and cross-sectional shape adapted for sensing the viscosity of a fluid. A lead-in rod 12 provides a torsional wave input which propagates into the sensor body, producing an echo at the junction J of rod 12 with the top face or edge 201a of the sensor body, and producing another echo at the bottom face 201b. The signal trace detected at exciter coil 16 includes two corresponding echo signals, denoted A and B, with the echo spacing interval $t_{AB}$ equal to twice the end-to-end flight time of the wave in the sensor body. The coil 16 may be grounded to the rod 12 such that only one live wire need extend out to the electronic signal processing circuitry Further, instead of the illustrated magnetostrictive transducers, piezoelectric elements may be used to excite the appropriate mode at the desired operating frequency. The sensor body is formed as a thin circular cylindrical shell, having a null component of normal motion, so that there is no $I_{f,i}$ coupling. From this signal trace, a signal processing front end and arithmetical processor of conventional design compute the fluid viscosity, using equations (2) and (4) and the measured $t_{AB}$.

According to one aspect of applicant's invention, a viscosity sensor has a circular cross-section at each point along its sensing length, but has a surface area that increases its viscous interaction with the fluid. This may be achieved by having the fluid-contacting surface threaded, which may increase the surface by two-fold or more without adversely altering the sensor impedance. Alternatively, a uniformly roughened surface preferably having a surface feature size less than the fluid's shear layer thickness, or a fractal surface may be used. In each of these embodiments, the amplitude of a torsional wave propagated in the sensor diminishes monotonically along the length of the sensor in contact with the fluid.

FIG. 3B shows a second sensor 102 according to the invention having a torsional wave guiding sensor body 202 of diamond cross-section, which applicant has found to be especially suited as a fluid density sensor. In this case the flight time $t_{A'B'}$ is significantly lengthened due to interaction of the torsional motion of the guide and the surrounding fluid. The flight time $t_{A'B'}$ together with equations (2) and (3) yields a direct measure of fluid density $\rho f$ in the case of an inviscid fluid. For other fluids, the viscous contribution may be corrected using the viscosity measurement provided by a viscosity sensor such as that of FIG. 3A. Applicant has found that sensors having aspect ratios near to three are easily formed by milling, by turning followed by straightening and annealing, or for large quantities, by drawing.

Figure 3C:
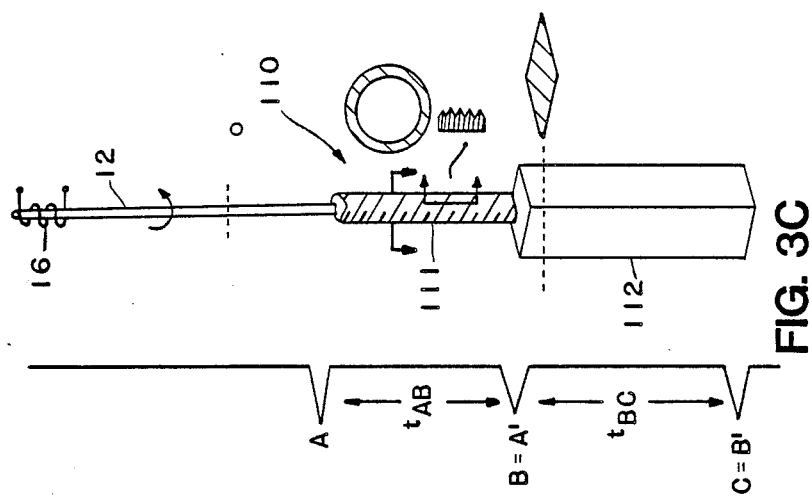
FIG. 3C shows a third embodiment of the invention optimized for simultaneously sensing different fluid characteristics.

FIG. 3C illustrates a presently preferred sensor embodiment 110 according to the invention, in which a single sensor body has two portions 111, 112 of different cross-section which serve as wave guides for a wave provided by a common lead-in rod 12. As illustrated, the first portion 111 is a thin cylindrical shell that is similar to the sensor body 101 of FIG. 3A, but is threaded along its outer surface. This construction increases the surface area over that of the simple cylinder of FIG. 3A, thus increasing the sensitivity to fluid viscosity, while presenting a constant impedance along the length of body 111 so that the torsional wave is not scattered or attenuated. The second portion 112 of sensor 110 is a diamond-section sensor body, like body 102 of FIG. 3B.

In this embodiment, a single coil 16 senses three echos A, B, C which provide two distinct time delay measurements $t_{AB}$ and $t_{BC}$. Because of the direct viscosity and density dependence of the sensor body portions, these two intervals provide sufficient information for resolving fluid viscosity and density, and for correcting cross-terms to compute physical properties that are functions of these fluid characteristics. The constructions of FIG. 3A-3C advantageously require but a single lead-in opening in a conduit for installation.

The invention contemplates that other viscosity-sensitive cross sectional profiles may be substituted for sensor body 111, and other density-sensitive profiles for body 112. Also the order of the two body portions may be reversed. Impedance matching at the end of each sensor body is preferably effected, for example, by soldering a ring about an end of the sensor body 111, to obtain an appropriate coupling of the torsional wave with adequate levels of wave reflection and transmission, at frequencies in the range of about 100 kHz. If the lead-in or sensor body diameter is sufficiently large, e.g., five to ten millimeters diameter, then a larger ring may be formed on the sensor as a mounting flange and used to form a vacuum- or pressure-tight seal by well known mounting or packing techniques without adversely affecting the impedance.

Sensor bodies according to the invention exhibiting a strong torsional wave propagation dependence on the surrounding fluid density also exhibit a marked signal reflection when a torsional wave travelling in a non-immersed portion of the sensor reaches the fluid boundary. For example, a stainless steel sensor of diamond cross-section and aspect ratio of approximately three yields a reflection coefficient of about ten percent at a water/air interface. Accordingly, in a further embodiment of the invention, a straight density sensor extending down into a fluid body may be actuated to provide a fluid height measurement. Sensor bodies that are optimized to respond to fluid viscosity exhibit an amplitude damping which depends on the immersion length, and may thus be employed as fluid height sensors by measuring the amplitude of the return signal.

Preferably, sensor bodies according to the present invention have a low average density. A density under approximately five grams/cc may be useful for many liquids. Some suitable materials are titanium, anodized aluminum, graphite, and electroless nickel-plated graphite. Stainless steel sensors are suitable for many liquid applications, and conductive sensor bodies may advantageously allow complex systems to operate with few active electrical leads.

Figure 4:
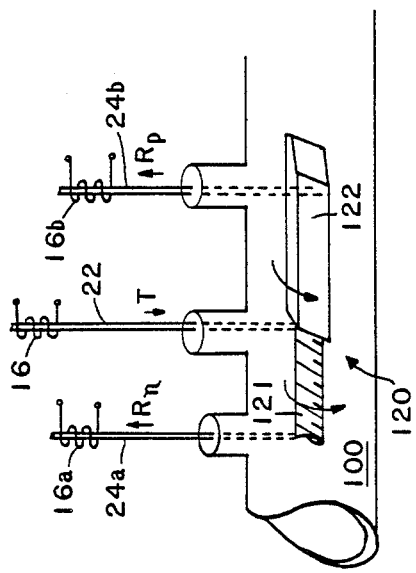
FIG. 4 shows another embodiment of a two-characteristic sensor according to the invention.

FIG. 4 shows another sensor 120 having two different torsional wave sensor body portions 121, 122 that are attached in series and subjected to excitation by a single lead-in rod 22 In this embodiment, the sensor bodies are parallel to the axis of a conduit 100, so that a longer sensor body may be accommodated, and so that the fluid density or velocity may be considered to be substantially uniform along the length of the sensor. Rod 22 is attached, e.g, by spot welding reinforced with a braze, to the middle of the sensor at an edge of the end of body 122 or of body 121. With this construction, a transmitted extensional wave T in the rod is simultaneously converted to a torsional wave in each body portion 121, 122. The two torsional waves travel in opposite directions. At the far end of each torsional waveguide sensor body, 121, 122, a respective lead-out rod 24a, 24b converts the received torsional wave to an extensional wave that travels up the lead-out rod and is sensed by a corresponding coil 16a, 16b. The construction of this commonly-excited and spatially separated two-body torsional wave sensor provides excellent wave isolation for the two sensing waves. This isolation is expected to enhance the achievable S/N ratio and time resolution, especially when the received signals are processed using multiple interrogation, signal correlation, or variance analysis techniques.

As in the sensor of FIG. 3C, the signal arriving through the illustrated diamond-shaped portion 122 provides a primarily density-dependent measure, and the signal arriving through the cylindrical portion 121 provides a viscosity measure.

Figure 5:
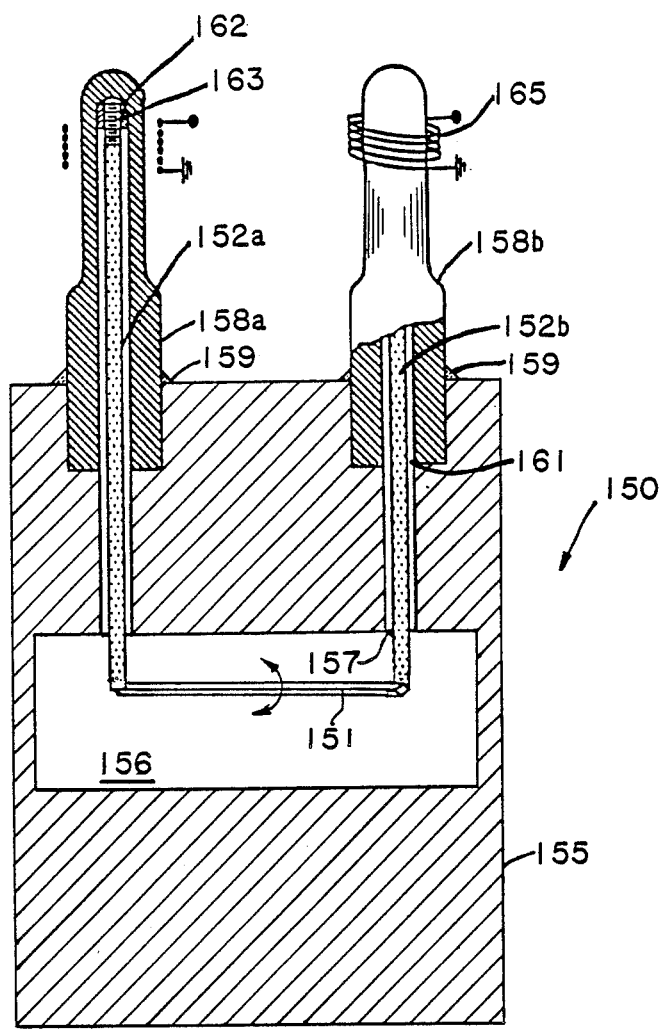
FIGS. 5, 5A show different embodiments of a torsional wave sensor mounted in a flow cell.

FIG. 5 shows a cross-sectional view through a flow measurement cell 150 employing a torsional wave sensor 151 with a $\rho$-sensitive body which is actuated by, and in turn actuates, rods 152a, 152b. The cell 150 has a thick body 155 with a central cavity or passage 156 which contains a very high pressure fluid. The exciter rods 152a, 152b are extensional wave exciter rods as in FIGS. 2, and 4. Each rod extends down a passage 157 through block 155, and is suspended from a plug 158a, 158b which is tightly fitted over the passage in a counterbored recess in the block and permanently secured thereto by a fluid-tight weld 159. A bore 161 within each plug accommodates the rod, and terminates in an upper threaded portion 162 having threads that only loosely mate with corresponding threads 163 on the rod 152a, 152b. In this manner the actuation rods are securely suspended, yet are acoustically decoupled from the flow cell body so that ringing does not interfere with the torsional wave signal generation or detection. A coil 165 placed about the outside of each plug actuates the rods. The plugs are formed of a non-magnetic material of suitable strength, such as SS304 or SS316.

Figure 5A:
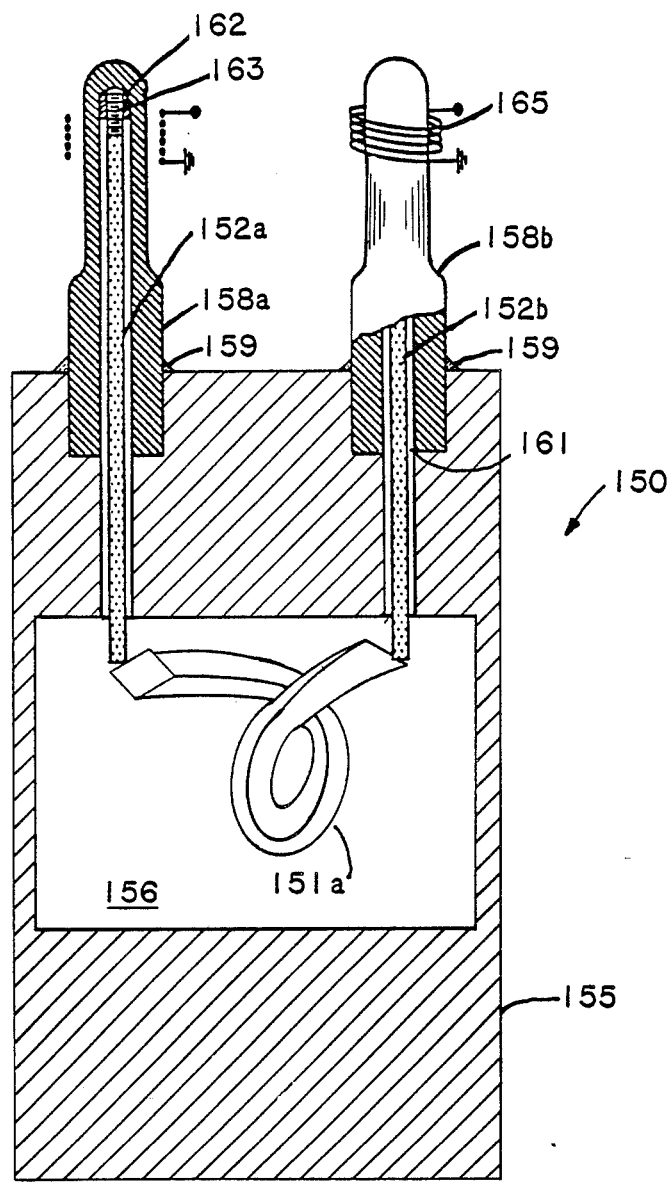

FIG. 5A shows a variation of this construction, wherein the torsional waveguide sensing element 151a is diamond cross section waveguide which is curved into a cylindrical helix. This configuration permits a longer waveguide to be used in the small flowcell chamber, enhancing sensitivity.

FIG. 6 shows another flow measurement system wherein a torsional waveguide sensor 181 with exciter/lead-out rods 182a 182b is positioned in a flow cell 180 of defined geometry, and wherein a pair ultrasonic transducers 184, 185 are further placed at the ends of the flow cell to launch and receive longitudinal (compressional) ultrasonic wave energy through fluid flowing in the cell. Transducers 184, 185 are actuated with an extensional wave by coils 16 about magnetostrictive rod ends 184a, 185a, and each transducer has a tapered body portion 184b, 185b which serves to match impedance to the larger end face that launches a sensing wave within the fluid. A relatively thin ring or mounting flange 186 (FIG. 6A) may be machined on the large portion, and used with an 0-ring seal or packing, or sealed by metal-to-metal pressure contact to provide a sealed through passage with little echo generation or coupling into the pipe body.

Also shown in FIG. 6, on the transducer rod 182a is a damping structure 178 which serves to eliminate spurious echoes from the rod. Such a damping structure is preferably provided on each extensional wave exciter or sensing rod; the rods may be extended beyond their junction with the sensor body 181, and a damping structure may be provided on each end of the rod. Structure 178 is preferably formed of a material such as a tungsten-loaded epoxy and has a characteristic impedance comparable to that of the rod but a sound speed lower than that of the rod. As shown, a preferred shape tapers outwardly to a diameter several times that of the rod, over a distance of one or more wavelengths.

In many applications it may be desirable to measure characteristics of a moving or stationary fluid that vary throughout the fluid body. This is achieved by a system according to the invention utilizing an array of torsional wave sensors. In compressible fluids, or with fluid masses that span extreme pressure or varying temperature ranges as in outdoor tanks, or under storage conditions close to a phase or state transition of a fluid, such an array of density sensors according to the invention is an effective means of quantifying the mass, or mass flow rate of a fluid. In a container of a cryofluid such as a hydrogen slush, or in a tank of aircraft fuel, a density profiling measurement may be effected in order to accurately measure its contents under whatever local conditions prevail. Another application of such density profiling is to monitor the distribution of dissolved salt concentrations in a system such as a thermal pump system.

Figure 7:
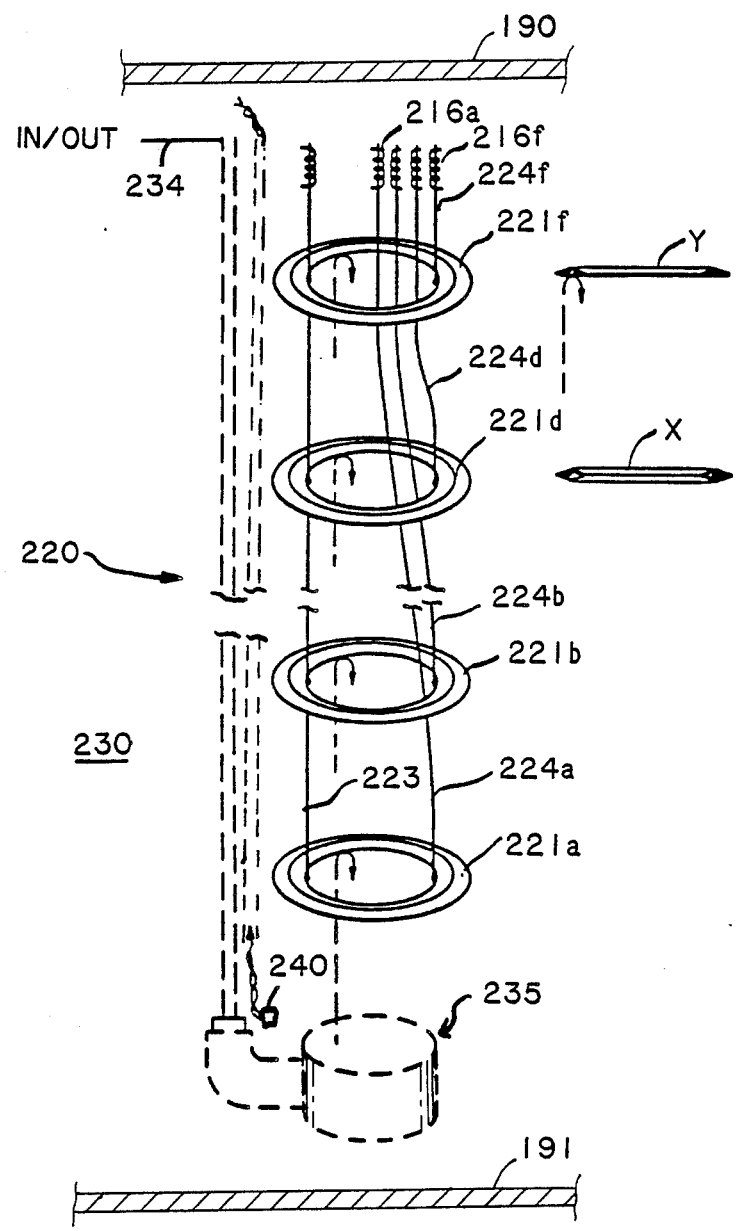
FIG. 7 shows a density profiling system which senses multiple parameters.

FIG. 7 illustrates one embodiment of a system 220 for measuring such a density profile. For purposes of illustration, the system is shown installed in an aircraft fuel tank wherein the fuel occupies the space between upper and lower wing surfaces 190, 191. In this system, a plurality of ring-shaped waveguides 221a,...221f are suspended at known vertical height locations and spacings within the tank interior 230, and are connected by a common exciter rod 223 which, as in the embodiment of FIG. 4, is rigidly attached to an edge of each ring for transmitting an extensional wave and converting it to a torsional wave in the ring. A plurality of lead-out rods 224a,...224f lead out the wave energy from diametrically opposed points of each ring, and coils 216a,...216f convert the wave energy to an electrical signal trace. An anti-sloshing well or other wall structure (not shown) preferably surrounds the sensor assembly to provide a relatively stable or slowing varying fuel level about the assembly. A relatively flexible and light plastic cage may also be provided to support the rings of the assembly in position without coupling them acoustically. Alternatively or additionally, loosely-fitted threaded rods may be passed through aligned holes tapped in the thicker central portion of each ring to Precisely control the ring spacing without acoustically coupling the different rings.

With this transducer assembly, the spacing of the return signals provides a direct measure of the fluid density at each height location. An abrupt discontinuity in torsional wave velocity will occur when the fluid level falls below a ring, thus also providing a rough measure of fluid height H.

Generally, the foregoing H and $\rho$ parameters may be insufficient to fully characterize the energy content or other technical aspects of the fuel mass M in an aircraft fuel tank, if the hydrocarbon composition of the fuel is not precisely known. The system 220 therefore preferably includes an independent acoustic wave transducer 235 and a temperature sensor 240 for effecting additional measurements to resolve these variables.

As shown, transducer 235 receives an electrical pulse on line 234 and launches an ultrasonic burst which is reflected from each of the rings 221a,...221f. Transducer 235 converts these echos to an output signal on line 234 that is processed in a conventional manner to determine the speed of propagation c in the fluid. Each of the P-sensor rings may be a diamond cross-section, as illustrated in the section detail "X". Preferably, however, at least some of the $\rho$-sensor rings have their bottom face modified so as to provide a better-defined echo to transducer 235. Section detail "Y" shows a flattened-diamond transducer section suitable for this purpose.

Also shown in FIG. 7 is a temperature sensor 240, which measures the temperature T of the fluid at one location. The multi-reflector density Profiling system of FIG. 7 provides a fuel mass measure as follows. First, the measure of c and T at one point yields a unique indication of fuel type or mixture of fuel types. This may be obtained by a look-up procedure from known data charts for common aircraft fuels, such as JP-3, kerosene, aviation gas and the like. For a given fuel, the temperature dependence of both $\rho$ and c is known. Thus, the further measurement of either a $\rho$-profile via torsional wave propagation in waveguides 221 or a c-profile by reflection of a fluid-propagation wave from those waveguides, together with the predetermined tank geometry, provides a measure of these properties of the fuel mass. An in-flight fuel gauging system may additionally utilize data on aircraft attitude, pitch, roll, yaw and center of gravity to provide more accurate computations.

In the particular case of fuel gauging in an airplane wing tank, where it is desirable to minimize the number of electrical wires, it is advantageous to have as few leads as possible to the gauging system. Applicant has developed a system having only one pair of through wires, which uses local passband filtering to separate signals for the different ultrasonic transducers. It will be understood that if the liquid is unsettled because of in-flight maneuvers other than routine cruising, suitable empirically ascertainable corrections must also be applied as functions of roll, pitch, yaw and accelerations, and in that case it is desirable to measure the fluid height at more than one location in the fuel tank. Multiple sensor units may be used, each having its own leads.

Figure 8:
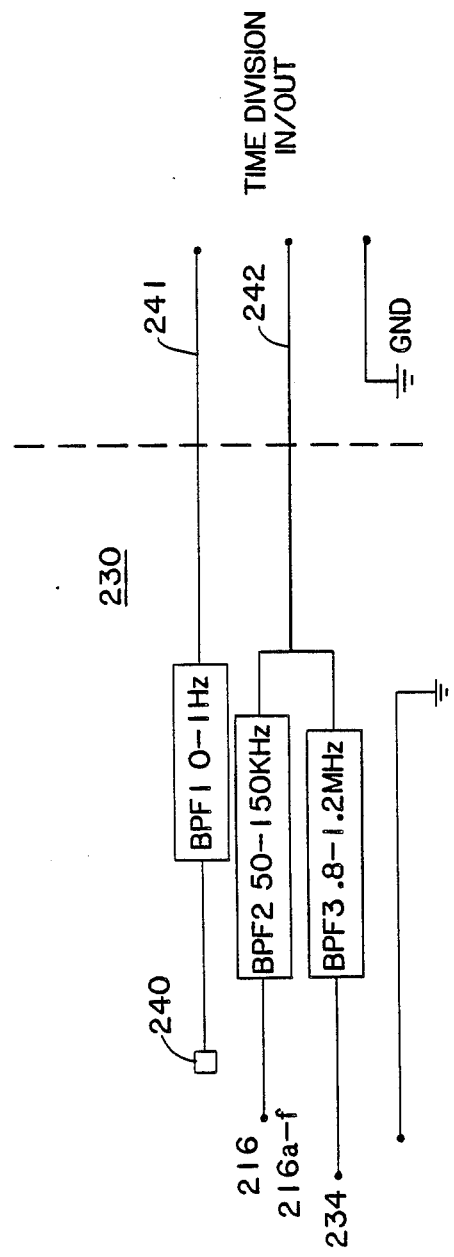
FIG. 8 shows a preferred electrical system for the density profiling system of FIG. 7.

FIG. 8 shows such a locally filtered wiring harness, wherein two leads 241, 242 pass through to the tank for carrying signals to multiple transducers. A first bandpass filter BPF1 that is a low pass filter with a passband of 0-1 Hz passes the DC temperature sensor signal on line 241, and a pair of bandpass filters BPF2, BPF3 are used to separate out the signals to and from the $\rho$sensors 221a-f and the transducer 235, respectively These signals are passed in a time division manner on line 242. The $\rho$ sensors operate with a nominal 100 kHz signal within the 50-150 kHz passband of BPF2, and the c-sensor operates with a 1 MHz signal within the higher 0.8-1.2 MHz passband of BPF3. A common ground is provided.

An advantage of a fluid sensor according to the present invention is that the torsional waveguide interaction with the fluid is to a large degree independent of conduit size and geometry, so long as there is maintained a certain minimal clearance from the conduit walls, and the sensor may therefore be installed in a wide range of field apparatus. For example, the embodiments of FIGS. 3A-3C may be installed with a single pipe opening. A spiral-shaped sensor similar to that illustrated in FIG. 5A may also be adapted for single-opening installation by mounting the sensor, with lead-in and lead-out rods, on a plug fitting of suitable diameter.

An additional advantage is that a guided torsional wave introduces relatively little interfering energy into a fluid system already having other ultrasonic pulses transmitted through the fluid. Moreover, the sensors may be quite small, e.g., one by three millimeters for a representative diamond-section $\rho$-sensor, so that they do not significantly scatter the other signals. Such sensors are thus well-adapted for incorporation in new system architectures. For industrial applications where ruggedness is of greater importance than light weight, larger cross sections may be used. In that case, the torsional wavelength is to be large compared to the maximum cross-sectional sensor dimension to avoid unwanted dispersive effects. It is noted that a principal feature of an optimized sensor according to the present invention is that it achieves effective fluid measurements with a sensor dimension well below the range of interfering dispersive effects that have previously limited the sensitivity or accuracy of torsional wave sensors.

Figure 9:
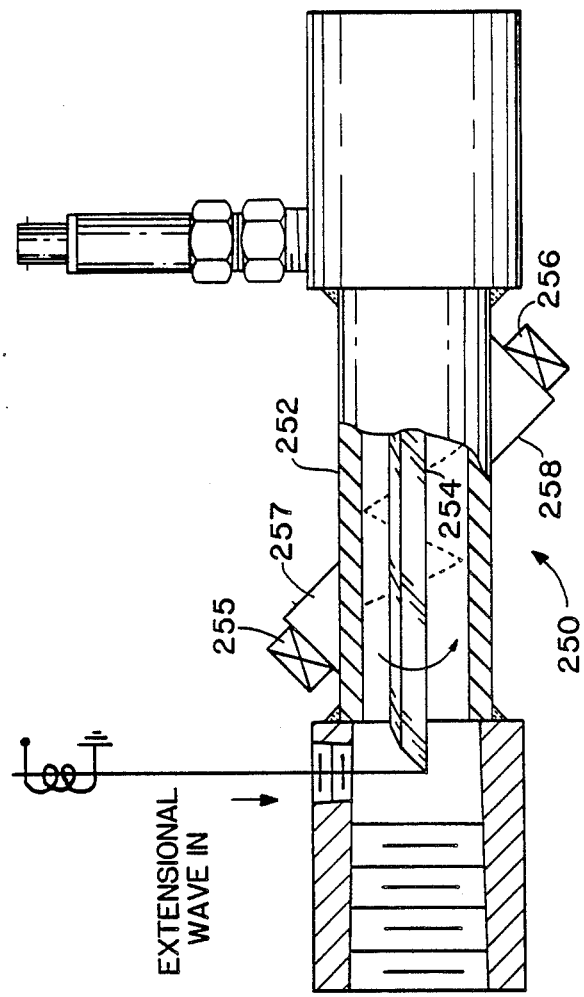
FIG. 9 shows a clamp-on mass flow sensing system.

FIG. 9 shows one such new system 250, which provides mass flow rate determination while minimizing pressure drop. A special flow segment 252 having a square internal cross section is connected in a fluid flow line. A density sensor 254 consisting of a torsional waveguide similar to that illustrated in FIG. 4 is mounted axially within segment 252, with an exciter rod and preferably a separate lead-out rod (not numbered) accommodated by suitable pipe fittings and packing Two clamp-on transducers 255, 256 with angled mounting blocks 257, 258 are positioned and clamped to the outside of the conduit to launch and receive an ultrasonic wave which follows a zig-zag reflection path to provide a velocity dependent transit time measurement. A more detailed discussion of such clamp-on flow velocity sensing may be found in U.S. Pat. No. 3,906,791. Preferably transducers 255, 256 launch and receive counterpropagating waves.

In operation, the system 250 derives a velocity measurement from the signal traces of transducers 255, 256, and a density measurement from the trace of torsional waveguide 254. The two interrogation modes operate in distinct frequency ranges (100 kHz vs. 1 MHz) and are physically and acoustically substantially independent. The measured velocity and density values are then multiplied, and corrected by a factor K which corrects for flow profile, scale and meter calibration, to produce a mass flow output value.

In a preferred variation of the system of FIG. 9, the specially-fabricated square conduit 252 is replaced by a conventional round pipe conduit to the V transducers are mounted externally and removably. Removability may be enhanced by using a fluid, grease, resilient (such as urethane, silicone rubber, or neoprene), or thermosetting (e.g., wax) couplant together with a magnetic clamp, mounting strap or velcro-latched belt to secure the transducer assembly. Two transducers may be clamped to a common pipe-mounting shoe in some embodiments. In such cases preferably a damping material, such as a tungsten-loaded epoxy having an acoustic impedance comparable to that of the shoe, is attached to the shoe or introduced into a cavity in the shoe between the transducers to reduce crosstalk.

Figure 10:
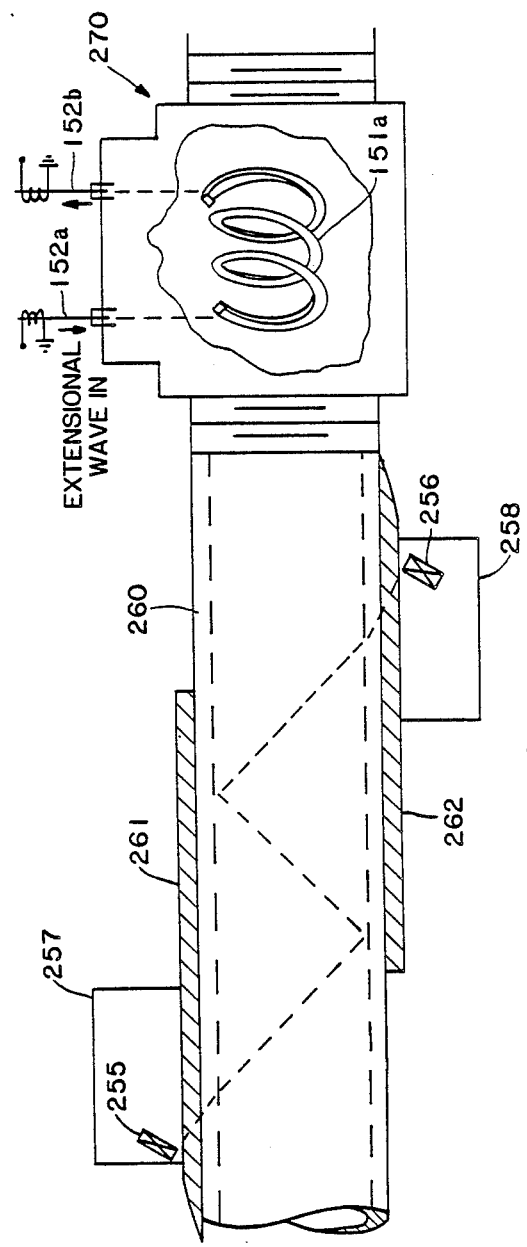

FIG. 10 shows such a system, with corresponding elements numbered identically to those of FIG. 5A, 9 employing a round pipe 260. In this embodiment, transducers 255, 256 with wedge blocks 257, 258 are clamped to a pair of shoes 261, 262 that provide a flat face to hold transducers at the correct angle to launch obliquely refracted waves into the fluid.

When this geometry is employed on pipes of different sizes, it would be desirable to eliminate variations in propagation associated with different wall thicknesses and different pipe curvatures. Under applicable standards, "standard" pipes of carbon steel, alloy steel and stainless steel exhibit the following wall thicknesses:

TABLE 1
Nominal wall thicknesses and shoe thicknesses for standard pipe.

| Nominal Pipe Diameter, Inches | | "Standard" Wall Thickness, Inches | Y, Inches |
|---|---|---|---|
| 2 | | .154 | .221 |
| 3 | | .216 | .159 |
| 4 | | .237 | .138 |
| 6 | | .280 | .095 |
| 8 | | .322 | .053 |
| 10 | | .365 | .010 |
| 12 | 24 | .375 | 0 |
| 14 | 26 | .375 | 0 |
| 16 | 28 | .375 | 0 |
| 18 | 30 | .375 | 0 |
| 20 | 32 | .375 | 0 |
| 22 | 34 | .375 | 0 |
| | 36 | .375 | 0 |

Accordingly, in a further preferred embodiment of a mass flowmeter of FIG. 10, the velocity sensing portion is constructed as shown in the views of FIGS. 11A–C. Here a shoe has been coupled or bonded to the pipe in a region under each of the two velocity clamp-on contrapropagation transducers. The thickness of the shoe, Y, is selected so that when added to the pipe wall thickness W, it yields a constant total thickness $W+Y$. A useful total is $W+Y=0.375$ inches because this locally converts all pipes in Table 1 to the same thickness as the standard thickness of pipes of 12 to 36 inch diameter. Thus, according to this aspect of the invention, for each pipe diameter, an adapter shoe is provided having a contact face conforming to the pipe outer diameter and having a minimum thickness dimension Y such that the pipe wall thickness is K-Y, where K is illustratively the constant thickness .375 inches. In practice a total thickness of one centimeter is preferred, so that the adapter shoe for the common larger pipe sizes does not have an excessively thin web.

FIGS. 11A–11C show end, side and perspective views, respectively of such a shoe 261. As shown, shoe 261 has a curved bottom face 265 which conforms to the pipe outer diameter so that energy transmission between the transducer element and the fluid is sufficiently great. The transducer wedge is mounted directly over this pipe-contacting portion and may extend over part or all of the shoe. A cut-out or relief portion 267 midway along the length of the shoe decouples a portion of the shoe from the pipe, and a tapered end section 269 of the shoe provides a gradual impedance transformation that controls signals, i.e., largely prevents echoing from the tapered end of the shoe.

FIG. 11C, in addition to showing a perspective view of the shoe 261, illustrates a preferred embodiment of a wedge 266 for mounting a piezoelectric transducer to generate Rayleigh-like waves. Wedge 266 is formed of one-inch square brass stock and has a transducer-mounting end face 268 formed at a $\pi/4$ angle to the face plane, so as to launch waves at an angle into the brass wedge. The brass material of wedge 266 propagates shear waves at a lower speed than the wave velocity in steel or SS pipe, so that Rayleigh-like waves are launched at an appropriate angle into the conduit. Preferably the length of wedge 266 is approximately that of the main body of shoe 261, to maintain constant boundary conditions and thereby limit or control the plate modes.

As further shown in FIG. 10, the clamp-on velocity segment 260 may be serially connected to a $p$-sensor cell 270, which contains a spiral-shaped or similar torsional waveguide of diamond-like cross section, such as the sensor of FIG. 5A. As shown, the torsional sensor presents a negligible flow obstruction, in part owing to the diamond knife-edge and its orientation with its major aspect dimension parallel to the flow.

Applicant observes that previously shoes have been added to pipes to accommodate clamp-on transducers. In earlier uses, however, the primary purpose of the shoe was to create a flat surface for ease of coupling, at a reproducible location. In the present instance, the shoe thickness is chosen to compensate for either the nominal pipe thickness using values in Table 1, or the actual pipe thickness based on a field measurement of the pipe wall thickness, which may vary from the listed nominal dimension. Further, the present shoes preferably are of constant width, e.g., 0.25 or 0.50 inches wide, over most of their length, to convert different pipes to geometries conducive to reproducible waveform and wave propagation characteristics.

Using this embodiment, flow in pipes is interrogated using longitudinal, shear, Rayleigh-like or Lamb waves in the pipe wall, for example. For a Lamb wave, the phase velocity is generally a function of the frequency-thickness product. Therefore, by making $W+Y=$ constant with a shoe formed of material having acoustical properties close to those of the pipe, one can use a given frequency Lamb wave on many different pipes and yet enjoy the benefit of essentially one phase velocity A further benefit of this shoe construction is obtained with Lamb or other plate waves, e.g., Rayleigh-like surface waves as described in applicant Lynnworth's U.S. Pat. No. 4,735,097, in that the abrupt change in geometry at the end of the shoe tends to block or reflect pipe-borne energy that might otherwise interfere with the accurate reception of the liquid-borne signal.

At the outboard ends of the shoe a gradual thinning of the Y dimension down towards zero provides a harmless escape path for energy that would otherwise remain trapped for a while in the shoe. For best results the shoe is made of the same material as the pipe, but reasonable results are obtainable using a SS304 shoe on pipes of carbon steel, SS316 or SS304. Similar performance is expected with other alloys of similar density and sound speed. The wedge may contact part or all of the shoe, depending on the desired boundary conditions, and other factors. Energy is coupled across the wedge/shoe and shoe/pipe interfaces by solid or non-rigid couplants depending in part on the particular wave being utilized in the pipe wall.

FIG. 12 shows yet another system 270 wherein a sensor according to the invention has a cross-section configured for torsional wave propagation that is highly interactive with a surrounding fluid. In this system, a large vat or tank 272 of height K of known geometry contains a fluid 274 that extends to an air-fluid interface at height H. A torsional waveguide 278 of optimized (e.g., diamond) cross section extends from an access port at the bottom of the tank vertically upward. An exciter/sensor coil 16 at the bottom is actuated by a pulser/receiver intervalometer 17.

The waveguide 278 has a central portion 280 extending over at least the range of heights encompassing the expected level of the fluid-air interface in normal use. Preferably the waveguide is formed of a single piece or rod of material, with the lower portion extending from coil 16 being of circular section, and the central portion being formed into a density-sensitive cross-section. The uppermost portion 283 above the expected fluid level may also have a circular section. Between portion 280 and the differently-shaped portions 281, 283 a gradual transition in shape is provided, which may extend over a length greater than one torsional wavelength, to minimize unwanted reflections.

A signal trace 290 illustrates the relation of the interface echo and end echo signals. The interface echo time $t_1$ provides a measure of fluid density, while the interval $t_2-t_1$ provides a measure of the unfilled height K-H of the tank.

Figure 13:
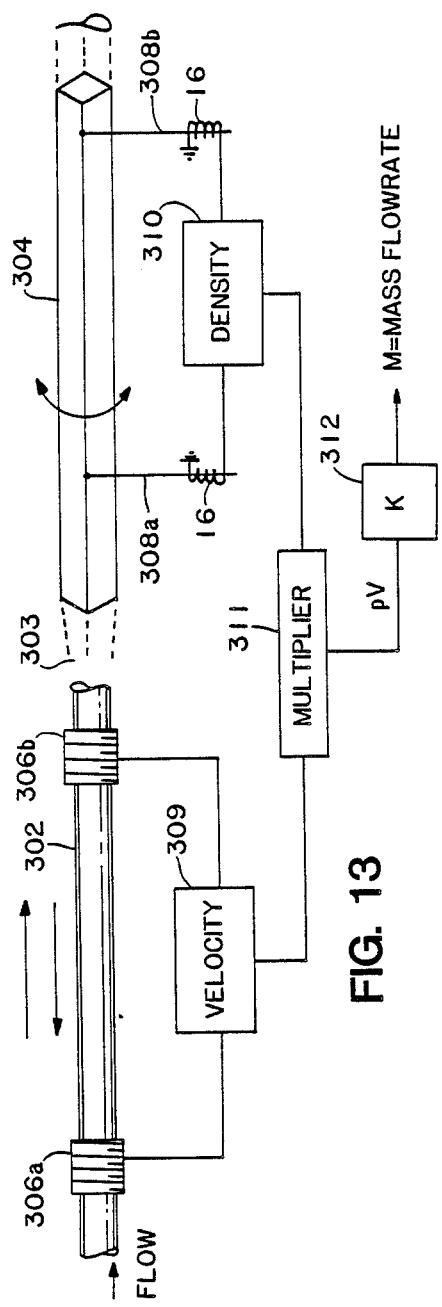
FIG. 13 shows a two-component sensor according to the invention configured as a process flow conduit.

FIG. 13 shows yet another system 300 of the present invention including a density sensor of optimized cross-section. In this embodiment, first and second conduit portions 302, 304 are provided in spaced-apart flow series, with an intermediate connecting portion 303. First conduit portion 302 is a somewhat flexible conduit, formed, for example, of stainless steel tubing of one millimeter wall thickness as used in the chemical process industry. The second conduit portion 304 is a hollow-diamond or other $\rho$-sensitive conduit, much as described above. The intervening conduit 303 may be of arbitrary shape, its function being to contain the fluid without introducing interfering acoustic coupling or echos.

In this embodiment of a system, low-order flexural wave energy is propagated in the first conduit 302. Preferably counterpropagating flexural waves are launched by a pair of transducers 306a, 306b placed at a known spacing at opposed ends of the conduit 302. Suitable transducer mechanisms and some discussion of flexural wave fluid interactions may be found in the article "A Guided Acoustic Wave Liquid Level Sensor", of E. Dieulesaint, D. Royer, 0. Legras and F. Boubenider, in IEEE 1987 Ultrasonics Symposium Proceedings, B. R. McAvoy, Ed. Vol. 1 pp. 569–572. The strong fluid-waveguide interaction is utilized in the system of FIG. 13 to detect fluid velocity by counterpropagating low order flexural waves in a thin-walled conduit 302. Conduit 304 is a hollow diamond- or other $\rho$-sensitive conduit section that is subjected to a torsional wave and sensed by exciter/sensor rods 308a, 308b. Processing units 309, 310 produce velocity and density measures that are multiplied by a multiplier 311 and are then corrected by a system meter factor K that corrects for scale, flow profile and calibration, to produce a mass flow output M. The various units 309, 310, 311 312 may be implemented with a single signal processing/intervalometer front end running different software processing modules to effect the required computations.

Figure 14:
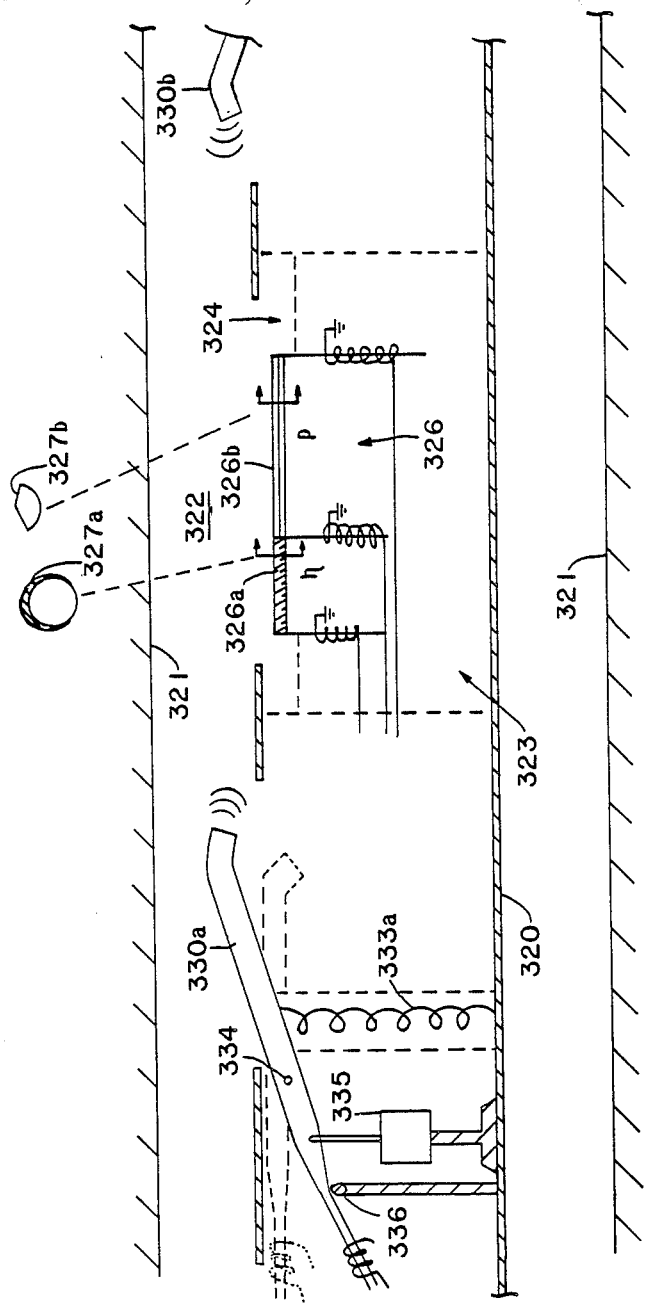
FIG. 14 shows a downhole sensor system.

FIG. 14 shows a system according to the invention adapted as a downhole fluid sensor tool. The tool 320 is mechanically centralized by conventional means within a borehole defined by walls 321, so that fluid fills an annular space 322 about the tool 320. Tool 320 has a diameter of under 43 millimeters, and houses a pair of opposable ultrasonic transducers 330a, 330b, which, as explained in greater detail below, swing out of the tool 320 to defined positions for effecting an ultrasonic signal measurement directly through the fluid in annulus 322. Between transducers 330a, 330b a fluids sampling flow segment 323 has an elongated uncoverable slot 324 in fluid communication with the annular region 322, which houses a two-profile flow sensor 326 for sensing density and viscosity of the borehole fluid.

The dual-element sensor 326 is substantially similar to the one illustrated in FIG. 4, and is positioned such that its threaded and diamond sensor body portions 326a, 326b lie in the slot 324 in the tool body and thereby interact with fluid passing along the annulus 322. Preferably, one or both of the sensor body portions is asymmetrical so as to preferentially interact with the fluid on its outer, annulus-facing side, as indicated in the detailed cross-sectional views 327a, 327b. Further, the lengths of the two sensor body parts preferably differ sufficiently in length so that the signals generated in their respective coils are disjointly separated in time. This allows the coils to be paralleled electrically into a single electrical lead, thereby reducing the required number of wires.

The V sensors 330a, 330b are similar to those denoted 184, 185 in FIG. 6, in that they taper from a narrow, magnetostrictive-actuated end to a wave-radiating face. The sensors 330a, 330b are spring-loaded by springs 333a, or are motor driven, such that once downhole, they can be deployed into the annular gap by pivoting outward from the tool body around a central point 334. The sensors have curved ends designed to survive accidental impacts with the sides of the borehole. The end faces are not necessarily parallel when so deployed, but if these end faces are small or comparable to the radiated wavelenth, they act much like point sources. This renders alignment non-critical. The effective radial position of the radiating end is indicated by an LVDT or other position sensor 335, or is controlled by a stop 336 which abuts the transducer's inner end. This determines a precise path length for the signals between transducers 330a, 330b in the annulus, given the fixed pivot point 334 and fixed probe geometry. This downhole system employs magnetostrictive actuators to develop and sense the sensing waves for all sensor/transducers 330a, 330b, 326a, 326b. The magnetostrictive elements have a Curie temperature in the range of 900° Celsius, which permits operation in an environment significantly above the 300° C. range of conventional piezoelectric sensing devices. The downhole system measures density, viscosity and velocity. Thus, in a particular well geometry where the hydraulic diameter D is known, the Reynolds number Re is readily calculated as $Re = \rho VD/\eta$.

The foregoing descriptions of sensors and the particular embodiments of systems shown in the figures have been presented to illustrate basic sensor embodiments and representative improved systems according to the invention. As such, the description is by way of example, and is not intended to limit the scope of the invention or patent rights claimed herein. With this description as a guide, further variations, modifications and improvements will occur to those of ordinary skill in the art, and such variations, modifications and improvements are considered to lie within the scope of the invention, as set forth in the claims appended hereto.

What is claimed is:

1. A sensor for sensing a physical property of a fluid, such sensor comprising a sensor body having a cross-sectional shape and a length, said sensor being mountable for immersion in a fluid for at least a portion of said length, and wherein said sensor is operative to propagate a torsional wave that interacts with the fluid along said portion to affect propagation of said wave in a manner functionally dependent on a physical property of the fluid, wherein said cross-sectional shape has an aspect ratio greater than one defined by major and minor axes, and has a contour lying within the contour of an ellipse of identical aspect ratio.

2. A sensor according to claim 1, wherein said cross-sectional shape is a diamond-like shape.

3. A sensor according to claim 2, wherein said cross-sectional shape has an aspect ratio of approximately three.

4. A sensor for sensing a physical property of a fluid, such sensor comprising a sensor body having at least a portion adapted for immersion in the fluid such that propagation of a torsional wave in said portion is modified by contact with the fluid, wherein a first part of said portion has a cross-sectional shape optimized to modify the propagation of said wave in functional dependence on a first property of said fluid, and a second part of said portion has a shape selected to modify the propagation of said wave in functional dependence on a second property of said fluid different from said first property.

5. A sensor according to claim 4, wherein said first and second properties are density and viscosity, respectively.

6. A sensor according to claim 5, wherein the first part has a diamond-like cross-sectional shape.

7. A sensor according to claim 6, wherein said first part is a double-edged blade.

8. A sensor according to claim 4, wherein said first and second parts sensed density and viscosity, and wherein the transit times of an interrogating torsional wave simultaneously launched in said parts differ by more than the period of the interrogating wave.

9. A sensor according to claim 8, wherein said sensor has a single electrical line connected to receive an electrical signal representative of wave energy propagated in both said first and second parts, in different time intervals.

10. A sensor for sensing a fluid property, wherein said sensor comprises a body portion adaPted for immersion in a fluid and for propagation of a torsional wave through the body, wherein the body Portion has a cross-sectional shape adapted to achieve a strong functional dependence of torsional wave velocity on fluid density, and a weak functional dependence on fluid viscosity.

11. A sensor according to claim 10, wherein said shape is further adapted to reflect wave energy directed through the fluid at said sensor.

12. A sensor for sensing a fluid property, wherein said sensor comprises a body portion adapted for immersion in a fluid and for propagation of a torsional wave through the body, wherein the body portion has a cross-sectional shape adapted to achieve a strong functional dependence of torsional wave propagation on fluid viscosity, and a weak functional dependence on fluid density.

13. A torsional waveguide for the propagation of torsional wave of wavelength $\lambda$ in a waveguide immersed in a fluid, wherein the waveguide couples wave energy to the fluid and propagation of the wave in the waveguide is dependent upon the physical characteristics of the fluid so that by sensing said wave propagation a characteristic of the fluid is ascertained, wherein the waveguide has a body of defined cross-sectional shape characterized by an inertia $I_s$, and further has a shaped contact surface in contact with said fluid such that the fluid exhibits a non-zero apparent inertia $I_f$ toward a torsional wave propagated in said waveguide, and $I_f$ is at least double $I_s$.

14. An improved waveguide for propagating a torsional wave of wavelength $\lambda$ in a waveguide immersed in a fluid such that interaction of said wave and the fluid provide an indication of a fluid physical characteristic, wherein said waveguide has a surface of non-circular cross-section contacting the fluid, and wherein the improvement comprises, for a given waveguide having a non-circular cross-section, the improvement wherein the cross-section of the waveguide is modified to decrease polar inertia.

15. A waveguide according to claim 14, having a central axis and a cross section modified by a mass distribution shifted close to said central axis.

16. A waveguide according to claim 14, having a fluid contacting surface modified to provide a surface with an increased normal component of a torsional wave motion along its length.

17. A waveguide according to claim 14, which is polyhedral.

18. A waveguide according to claim 17, which has a diamond cross section.

19. A waveguide according to claim 17, which has concave sides.

20. A system for the detection of fluid parameters, such system comprising
a sensor mounted for immersion along at least a portion of its length in a fluid,
wave initiating means for exciting a torsional wave in said sensor to propagate along the sensor,
detection means for detecting the propagated wave, and
processing means responsive to said detection means for determining a physical characteristic of the fluid,
wherein said sensor has a substantially uniform non-elliptical and non-rectangular geometric cross-sectional shape such that said torsional wave propagates as a guided wave in said sensor with a speed that varies primarily as function of inviscid coupling to the fluid.

21. A system according to claim 20, further comprising
a second sensor distinct from said sensor, having a different cross-sectional shape which responds to fluid viscosity, and wherein said processing means includes means responsive to said sensor for determining fluid viscosity.

22. A system according to claim 21, wherein said second sensor comprises a portion of said sensor having a substantially circular cross section.

23. A system according to claim 21, wherein said portion of said sensor has an enlarged fluid-contacting surface area greater than the area of a cylinder of the same cross section.

24. A system according to claim 20, wherein a portion of the cross-sectional shape is adapted to reflect wave energy transmitted in the fluid.

25. A system according to claim 20, further comprising
means for directing wave energy through said fluid at said sensor, and
means for detecting wave energy reflected from said sensor.

26. A system according to claim 20, wherein said sensor has a diamond-like cross-section.

27. A system according to claim 20, wherein said sensor is a conductive grounded sensor, and said system includes a single electrical lead interconnecting said sensor with said system.

28. A system according to claim 20, further comprising
an electrically operated transducer element distinct from said sensor, at least one local filter operative to separate electrical signals for said sensor and electrical signals for said transducer element, and a common lead-in wire to said local filter carrying electrical signals for both said sensor and said transducer element.

29. A system according to claim 20, wherein said sensor comprises a plurality of fixedly-mounted ring-shaped waveguides of diamond-like cross-section, said waveguides being commonly actuated by said wave-initiating means.

30. A system according to claim 29, further comprising means for propagating wave energy through the fluid to reflect from fixedly-mounted reflectors in said fluid to determine a fluid transit time, and wherein said detection and processing means detect and determine reflected wave energy and its transit time.

31. A system according to claim 20, and mounted in a downhole tool.

32. A system according to claim 31, further comprising a flow velocity sensor having a wave propagating tip movable to a position outside the tool for sensing borehole fluid, and means for determining the Reynolds number of the borehole fluid.

33. A system according to claim 32, wherein a said sensor is actuated by a magnetostrictive element having a Curie temperature above 300° Celsius.

34. A sensor as in claim 32, wherein said downhole tool has a diameter of under approximately forty-three millimeters.

35. A sensor system for the measurement of a fluid having first and second characteristics which interact in a functionally interdependent manner with sensor wave energy propagated in a physical sensing element, such sensor system comprising first and second sensor body portions having respective first and second cross-sectional shapes each adapted to propagate torsional wave energy in a respective one of said characteristics, whereby the detection of wave energy propagated in said first and second body portions provides sufficient information to calculate values of said first and second characteristics.

36. A sensor system according to claim 35, wherein a said sensor body portion has a polygonal cross section of aspect ratio greater than one and a shape adapted to respond strongly to fluid density.

37. A sensor system according to claim 35, wherein a said sensor body portion has an approximately circular cross section and has a surface adapted to respond primarily to fluid viscosity.

38. A sensor system according to claim 37, wherein said surface is threaded.

39. A sensor system according to claim 37, wherein said sensor body portion is hollow.

40. A sensor system according to claim 35, wherein at least one said sensor body portion is hollow.

41. A sensor system according to claim 40, wherein a said hollow sensor body portion is a fluid conduit.

42. A sensor system according to claim 35, wherein a said sensor body portion has a low average density.

43. A sensor system according to claim 42, wherein a said sensor body portion has a density under approximately five grams per cubic centimeter.

44. A sensor system according to claim 42, wherein a said sensor body includes one of the materials titanium, surface-treated aluminum, graphite, and electrodes nickel-plated graphite.

45. A sensor system according to claim 35, wherein the sensor is electrically conductive.

46. A sensor system according to claim 35, wherein said first and second sensor body portions are interconnected such that a common transducer excites both said body portions.

* * * * *

UNITED STATES PATENT AND TRADEMARK OFFICE
CERTIFICATE OF CORRECTION

PATENT NO. : 4,893,496
DATED : January 16, 1990
INVENTOR(S) : Bau, et. al.

It is certified that error appears in the above-identified patent and that said Letters Patent is hereby corrected as shown below:

Column 1, line 3, please replace "SYSTEMBackground of the Invention" with --SYSTEM Background of the Invention--.

Column 1, line 61, please replace "Objects and Summary of the Invention" with --

Objects and Summary of the Invention--.

Column 2, line 20, please replace "resPonsive" with --responsive--.

Column 2, line 35, please replace "Preferred" with --preferred--.

Column 2, line 47, please replace "tonian types. Brief Description of Drawings" with
--tonian types.

Brief Description of Drawings--.

Column 3, line 54, after "In" please insert --this--.

Column 3, line 64, after "signal" please insert --.--.

UNITED STATES PATENT AND TRADEMARK OFFICE
CERTIFICATE OF CORRECTION

PATENT NO. : 4,893,496
DATED : January 16, 1990
INVENTOR(S) : Bau et al.

Page 2 of 4

It is certified that error appears in the above-identified patent and that said Letters Patent is hereby corrected as shown below:

Column 4, line 21, before "the fluid" please replace "Is" with $--I_S--$.

Column 4, line 42, please replace "$K=°(D/I_S)$" with $--K = \sqrt{(D/I_S)}--$.

Column 4, line 43, after "rigidity" please insert --.--.

Column 4, line 46, after "time" please insert --.--.

Column 4, line 66, after "effects" please insert --.--.

Column 5, line 2, after "various" please insert --aspect--.

Column 5, line 6, please replace "Pressure-induced" with --pressure-induced--.

Column 5, line 14, before "The" please insert --.--.

Column 5, line 43, please replace "e" with --waveguide--.

Column 6, line 40, after "embodiments" please insert --.--.

Column 7, line 6, before "Further" please insert --.--.

Column 8, line 45, please replace "shOws" with --shows--.

UNITED STATES PATENT AND TRADEMARK OFFICE
CERTIFICATE OF CORRECTION

PATENT NO. : 4,893,496
DATED : January 16, 1990
INVENTOR(S) : Bau et al.

Page 3 of 4

It is certified that error appears in the above-identified patent and that said Letters Patent is hereby corrected as shown below:

Column 8, line 48, after "rod 22" please insert --.--.

Column 9, line 38, after "182a" please insert --,--.

Column 11, line 41, after "respectively" please insert --.--.

Column 17, line 9, please replace "optimized" with --selected--.

Column 17, line 33, please replace "adaPted" with --adapted--.

Column 17, line 35, please replace "Portion" with --portion--.

Column 20, line 2, before "respective" please insert --manner strongly functionally dependent on a--.

UNITED STATES PATENT AND TRADEMARK OFFICE
CERTIFICATE OF CORRECTION

PATENT NO. : 4,893,496
DATED : January 16, 1990
INVENTOR(S) : Bau, et. al.

It is certified that error appears in the above-identified patent and that said Letters Patent is hereby corrected as shown below:

Column 20, line 31, please replace "electrodes" with --electroless--.

Signed and Sealed this

First Day of September, 1992

Attest:

DOUGLAS B. COMER

Attesting Officer

Acting Commissioner of Patents and Trademarks